(12) United States Patent
Rigler et al.

(10) Patent No.: US 11,788,140 B2
(45) Date of Patent: *Oct. 17, 2023

(54) SINGLE MOLECULE ANALYSIS WITH HIGH ACCURACY

(71) Applicant: GNOTHIS HOLDING AG, Zug (CH)

(72) Inventors: Rudolf Rigler, Djursholm (SE); Lars Edman, Stockholm (SE)

(73) Assignee: Gnothis Holding AG, Cham (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/376,324

(22) Filed: Jul. 15, 2021

(65) Prior Publication Data

US 2022/0002800 A1 Jan. 6, 2022

Related U.S. Application Data

(62) Division of application No. 15/110,779, filed as application No. PCT/EP2015/050066 on Jan. 5, 2015, now Pat. No. 11,091,805.

(30) Foreign Application Priority Data

Jan. 10, 2014 (EP) .................. 14150807

(51) Int. Cl.
- *C12Q 1/6874* (2018.01)
- *C12Q 1/6837* (2018.01)
- *G01N 21/64* (2006.01)

(52) U.S. Cl.
CPC ......... *C12Q 1/6874* (2013.01); *C12Q 1/6837* (2013.01); *G01N 21/6428* (2013.01); *G01N 21/6452* (2013.01); *G01N 2021/6439* (2013.01)

(58) Field of Classification Search
CPC ............ C12Q 1/6874; C12Q 2563/107; C12Q 2565/507; C12Q 1/6837; G01N 2021/6439; G01N 21/6428; G01N 21/6452
See application file for complete search history.

(56) References Cited

U.S. PATENT DOCUMENTS

| 11,091,805 | B2* | 8/2021 | Rigler | .................. C12Q 1/6837 |
| 11,519,030 | B2* | 12/2022 | Rigler | .................. B01L 3/5085 |
| 2007/0206187 | A1 | 9/2007 | Lundquist et al. | |
| 2013/0157264 | A1 | 6/2013 | Obara et al. | |
| 2018/0187258 | A1 | 7/2018 | Rigler | |

FOREIGN PATENT DOCUMENTS

WO 2013131888 A1 9/2013

OTHER PUBLICATIONS

Ryan A. Colyer et al: "High-throughput FCS using an LCOS spatial light modulator and an 8×1 SPAD array", Biomedical Optics Express, vol. 1, No. 5, Nov. 15, 2010 (Nov. 15, 2010), pp. 1408-1431, XP055174601, ISSN: 2156-7085, DOI: 10.1364/80E.1.001408 Abstract; p. 1413, para. 2.3; p. 1414, 3rd para.; p. 1418, 2nd and 4th para.; fig. 3, 5.

Ivan Rech et al: "Toward single-molecule detection with very compact DNA sequencer based on single-photon avalanche diode array", Proceedings of SPIE, vol. 6862, Feb. 7, 2008 (Feb. 7, 2008), pp. 68620D-1, XP055174615, ISSN: 0277-786X, DOI: 10.1117/12.764508 abstract; p. 68620D-4, last para.; p. 68620D-6, para. 2. 4.

X. Michalet et al: "Development of new photon-counting detectors for single-molecule fluorescence microscopy", IEEE Photonics Journal, vol. 4, No. 6, Dec. 24, 2012 (Dec. 24, 2012), pp. 1-22, XP055174606, ISSN: 1943-0655, DOI: 10.1364/0E.20.005849 the whole document.

X. Michalet et al: "Supporting Information for Development of new photon-counting detectors for single-molecule fluorescence microscopy", IEEE Photonics Journal, Dec. 24, 2012 (Dec. 24, 2012), XP055174608, Retrieved from the Internet: URL:http://rstb.royalsocietypublishing.org/content/royptb/suppl/2012/12/14/rstb.2012.0035.DC1/rstb20120035suppl.pdf [retrieved on Mar. 6, 2015] the whole document.

Office Action dated Jul. 12, 2018, cited in European Application No. 15 700 025.8, 8 pgs.

Colyer et al., "High-throughput FCS using an LCOS spatial light modulator and an 8×1 SPAD array," Biomedical Optics Express, December, vol. 1, No. 5, pp. 1408-1431. (Year: 2010).

* cited by examiner

Primary Examiner — Young J Kim
(74) Attorney, Agent, or Firm — Rothwell, Figg, Ernst & Manbeck, P.C.

(57) ABSTRACT

The invention relates to a process for analysing single molecules, in particular for sequencing of single nucleic acid molecules.

27 Claims, 6 Drawing Sheets

Laser Point Matrix

Nanowells

R= 50 nm
H= 100 nm
V= 785 zL
1mol/V= 2,1 µM

Confocal Field
DNA strand kinked
No. of enzyme molecules undetermined

Evanescent Field

R= 100 nm
H= 50 nm
V= 523 zL
1mol/V= 3,2 µM

Objective TIRF Intensity
DNA strand straight
Single Enzyme molecule

SINGLE MOLECULE ANALYSIS WITH HIGH ACCURACY

This application is a divisional of U.S. Ser. No. 15/110,779 filed Jul. 11, 2016, which is a 35 U.S.C. 371 National Phase Entry Application from PCT/EP2015/050066, filed Jan. 5, 2015, which claims the benefit of European Patent Application No. 14150807.7 filed on Jan. 10, 2014, the disclosures of which are incorporated herein in their entirety by reference.

The invention relates to a process for analysing single molecules, in particular for sequencing of single nucleic acid molecules.

Sequencing of the human genome which consists of approx. $3 \times 10^9$ bases, or of the genome of other organisms and the determination and comparison of individual sequence variants requires the provision of sequencing methods which firstly are fast and secondly can be employed routinely and cost-effectively. Large efforts have been made in order to accelerate familiar sequencing methods, for example the enzymatic chain termination method according to Sanger et al. (Proc. Natl. Acad. Sci. USA 74 (1977), 5463), in particular by automation (Adams et al., Automated DNA Sequencing and Analysis (1994), New York, Academic Press).

The high demand for cost-efficient sequencing has driven the development of high-throughput sequencing technologies that parallelize the sequencing process producing a plurality of sequences concurrently. Examples of these sequencing technologies are massively parallel signature sequencing (Lynx Therapeutics), polony sequencing (Life Technologies), 454 pyrosequencing (Roche Diagnostics), illumina sequencing (Solexa Inc.), sequencing by ligation (Life Technologies), ion torrent semiconductor sequencing (Life Technologies) or DNA nanoball sequencing (Complete Genomics). These technologies allow rapid analysis of a consensus sequence in a nucleic acid population. Mutations existing in minority sequences in the nucleic acid population to be analysed, e.g. in a minority of cellular genomes, however, will not be detected since they are obscured by the majority of other sequences present in the population.

Another approach is single-molecule sequencing (Dorre et al., Bioimaging 5 (1997), 139-152), in which the sequencing of nucleic acids is carried out by progressive enzymatic degradation of fluorescently labelled single-stranded DNA molecules and by detection of the sequentially released monomeric molecules in a microstructure channel. This process has the advantage of only a single molecule of the target nucleic acid being sufficient for carrying out a sequence determination.

PCT/EP01/07462 discloses a multiplex sequencing process which comprises providing, in an immobilized form, nucleic acid molecules carrying a plurality of fluorescent labelling groups on a support and determining simultaneously the base sequence of a plurality of nucleic acid molecules on the basis of the time-dependent change, caused when nucleotide building blocks are cleaved off, in the fluorescence of said nucleic acid molecules or/and said cleaved-off nucleotide building blocks. According to WO 2003/052137, the sequence is determined by irradiating light into the support and generating an evanescent excitation field by way of internal reflection on the support surface in the region of the immobilized nucleic acid molecules.

WO 2006/013110 describes a multiplex sequencing process which comprises providing, in an immobilized form, nucleic acid-degrading and/or nucleic acid-synthesizing enzyme molecules, contacting the immobilized enzymes with free nucleic acid molecules and determining simultaneously the base sequence of a plurality of nucleic acid molecules on the basis of the time-dependent fluorescence change caused when nucleic acid building blocks are incorporated into and/or cleaved off from the nucleic acid molecules.

WO 2013/131888 discloses a process for parallel high-throughput sequencing of nucleic acid molecules, particularly in the single molecule, which involves the use of a circular nucleic acid template molecule.

Recently, single molecule sequencing technologies for determining the sequence of a single DNA strand have been developed, e.g. heliscope single molecule sequencing (Helicos Biosciences) or single molecule real time sequencing (Pacific Bioscience).

The approach of present commercial single-molecule DNA sequencing technologies involves a so-called consensus determination of a DNA sequence. By this means it is intended to provide an accurate (preferably 99.9% or better) determination of the sequence of a DNA fragment by the analysis of several similar DNA fragments and by the use of complex statistical algorithms to estimate the correct DNA sequence. These algorithms are based on the assumption that there exists only a single sequence in the sample to be analysed. Hence if there are minor sequence variants present in the sample that differ in their sequences from the other DNA molecules in the sample such minor sequence variants will not be considered but will be treated by the algorithm as "noise" or "error". If the sample contains a mixture of different DNA sequence variants at approximately the same concentrations, an algorithm-based analysis will not be able to conclude a "consensus" sequence and the result will be void (invalid). The use of a complex algorithm however is necessary to compensate that present commercially available single-molecule DNA sequencing technologies' have only a low primary accuracy of approximately 85-90%.

In order to overcome accuracy problems associated with prior sequencing processes, the present invention provides a single molecule sequencing process which achieves sufficient precision in order to allow analysis of individual strand mutations as well as their distribution in a population of DNA molecules.

Thus, the present invention provides a process and a device for analysing single molecules, particularly for analysing a plurality of single molecules, more particularly for sequencing single nucleic acid molecules comprising the following features:

- a support having at least one sample spot for positioning a single molecule to be analysed on a support,
- a light source, particularly a multipoint laser providing at least one illuminated volume element, e.g. a confocal volume element, at the position of the at least one single molecule on the support, and
- a detector, particularly a multipixel detector, which allows single photon detection from an individual single molecule on the support.

By means of an optical pathway between the light source, the support and the detector, the detection pixels on the detector, i.e. in the image plane, are optically projected onto the support, i.e. onto the object plane. Thereby, the size of the detection pixels in the image plane is magnified, e.g. 10-200 times, preferably 40-120 times as compared to the size of the optical projection of detection pixels on the support.

According to the present invention, a sample spot on the support is aligned to an optical projection of a single detection pixel, preferably to the center of the projection of a single detection pixel on the support. Alignment between the center of a sample spot and the center of a pixel projection is preferably provided with a tolerance of e.g. 5 nm or less, 2 nm or less or even 1 nm or less. The alignment may be provided by diffractive optical elements and/or adjustment elements. The positioning of the sample spots on the support and the optical projections of pixels on the support is such that the distance between individual sample spots on the support is preferably equivalent to the distance between the optical projections of pixels on the support. Thereby, crosstalk between signals from individual detector pixels is avoided and individual single molecules can be analysed with high accuracy, preferably with an accuracy of at least 99.0%, at least 99.3%, at least 99.6% or at least 99.9% with a single measurement and optionally up to 10, e.g. 1, 2, 3, 4 or 5 measurement repeats.

The present approach to do DNA sequencing is that of single-molecule DNA sequencing with primary accuracy of preferably at least 99.9%. Since the method is highly accurate each single DNA molecule's sequence is read correctly and there is no need for more than perhaps few, e.g. 1, 2 or 3 repeated measurements of each individual DNA molecule to achieve almost 100% accuracy. The concept of a "consensus" sequence is not applicable for the present DNA sequencing and there is no need for complex algorithms to interpret the measurement data.

Provided that the primary accuracy (i.e. the probability of successful identification of a single base) is p (0<p<1) the average number of sequencing rounds needed to achieve a sequencing result with an accuracy of ε (0<ε<1) when sequencing a DNA fragment of length N base pairs is $$\text{Sequencing rounds needed} = \frac{\text{Log}(1-\varepsilon)}{\text{Log}(1-p^N)}. \tag{1}$$

Below, in Table 1, the equation (1) is used to calculate the number of needed sequencing rounds for a DNA fragment of length 100 base pairs and 1000 base pairs, respectively.

TABLE 1

Comparison summary of present technology versus other DNA single-molecule sequencing technologies

|  | Primary accuracy (probability of correct identification of a single base) | Analysis of variations between individual DNA molecules | Sequencing rounds needed until 100 bases DNA fragment is read at 99.9% accuracy | Sequencing rounds needed until 1000 bases DNA fragment is read at 99.9% accuracy |
| --- | --- | --- | --- | --- |
| Present invention | 99.9% | Yes | 3 | 15 |
| Other DNA single-molecule sequencing technologies | 85% | No | 78 966 766 | Infinity (too large number to be presented) |

Calculation of Number of Re-Sequencing Rounds Needed to Get an Accurate Read-Out (Derivation of Equation 1)

Define p as the primary accuracy=probability of successful identification of a single base. p is a real valued number defined in the closed interval from zero to unity.

N is the number of bases in the DNA molecule to be sequenced. N is a positive integer.

$p_{seq}$ is the probability that the whole sequence of N bases is correctly read. $p_{seq}$ is a real valued number defined in the closed interval from zero to unity. Then:

$$p_{seq} = p^N \tag{2}$$

Define r as the number of times the method will analyse and read out the DNA sequence form a given DNA molecule. R is a positive integer. R may also be referred to as "the number of re-sequencing rounds".

Then the probability E that at least one read-out will be correct, out of r sequencing rounds performed, is given by P (at least one correct read-out out of r sequencing rounds performed)=

$$\sum_{i=1}^{r} \frac{r!}{(r-i)!i!} p_{seq}^i (1-p_{seq})^{r-i} = \tag{3}$$

1 − P(zero correct read − out out of r sequencing rounds performed) = 1 − $(1-p_{seq})^r = \varepsilon$.

ε is a real valued number in the closed interval between zero and unity.

Insertion of equation (2) in Equation (3) yields
ε=1−(1−$p^N$)$^r$ which is equivalent to $$1-\varepsilon = (1-p^N)^r \tag{4}$$

Furthermore by applying the logarithm function to both sides of equation (4) yields
ε=1−(1−$p^N$)$^r$ which is equivalent to $$1=\varepsilon-(1-p^N)^r \tag{4}$$

Furthermore by applying the logarithm function to both sides of equation (4) yields $$\log(1-\varepsilon) = \log((1-p^N)^r) \text{ which is equivalent to } \log(1-\varepsilon) = \tag{5 and 1}$$

$$r\log((1-p^N)) \text{ which is equivalent to } r = \frac{\log(1-\varepsilon)}{\log((1-p^N))}.$$

The present invention relates to a process for analysing a single molecule, comprising the following steps:
(a) providing at least one single molecule to be analysed positioned at an individual sample spot on a support, wherein said spot has a diameter in the range of about 1-20 nm and the distance between each individual spot is at least about 2 times, preferably about 3-10 times the diameter of the spot,
(b) individually illuminating a single molecule at an individual sample spot with a light source, wherein said light source provides at least one illuminated volume element at the sample spot,
(c) individually detecting light from said single molecule with a light detector comprising at least one detection pixel, wherein said detection pixel on the detector has a diameter in the range of about 0.5 μm-50 μm and the distance between each detection pixel is at least about 2 times, preferably about 3-10 times, in particular at least 3 times or at least 5 times the diameter of the detection pixel, and
(d) correlating the detected light from an individual detection pixel with an event associated with a single molecule positioned on an individual spot,
wherein an optical projection of a detection pixel on the support has a diameter in the range of about 100 nm-5 μm and wherein an individual sample spot is aligned to the projection of a single detection pixel on the support, particularly to the center of the projection of a single detection pixel on the support.

The present invention particularly relates to a process for analysing single molecules, comprising the following steps:
(a) providing a plurality of single molecules to be analysed, each positioned at an individual sample spot on a support, wherein said spots have a diameter in the range of about 1-20 nm and the distance between individual spots is at least about 2 times, preferably about 3-10 times the diameter of the spot,
(b) individually illuminating single molecules at individual sample spots with a light source, wherein said light source provides a plurality of individual illuminated volume elements at the sample spots,
(c) individually detecting light emitted from said single molecules with a light detector, wherein the light detector comprises a plurality of detection pixels, wherein said detection pixels on the detector have a diameter in the range of about 0.5 μm-50 μm and the distance between said detection pixels is at least about 2 times, preferably about 3-10 times, in particular at least 3 times or at least 5 times the diameter of the detection pixel, and
(d) correlating the detected light from an individual detection pixel with an event associated with a single molecule positioned on an individual spot,
wherein an optical projection of a detection pixel on the support has a diameter in the range of about 100 nm-5 μm and wherein an individual sample spot is aligned to the projection of a single detection pixel on the support, particularly to the center of the projection of a single detection pixel on the support.

The process of the invention relates to the analysis of a single molecule, particularly to the parallel analysis of a plurality of single molecules. It is suitable for detecting interactions, e.g. binding between single molecules and/or reactions, e.g. elongation or degradation of single molecules. Particularly, the process of the invention relates to the sequencing of single nucleic acid molecules.

In the present invention, a support is provided comprising at least one sample spot and particularly a plurality of individual sample spots for positioning single molecules to be analysed thereon. The spots may have a diameter in the range of about 1-20 nm, e.g. about 2-15 nm or about 4-12 nm. In order to avoid crosstalk between individual spots, the distance between the centers of individual sample spots on the support (i.e. the sample spot distance) is preferably at least about 2 times, at least about 3 times, at least about 5 times more, at least about 10 times, such as from about 3-10 times, or about 20 to 500 times, e.g. about 50 to 400 times the size of the spot diameter. The sample spot distance is preferably from about 50 nm-5000 nm, e.g. about 150-3000 nm.

The single molecule to be analysed may be bound to the surface of the support. In other embodiments, the single molecule to be analysed is not bound to the support surface at the sample spot, but present in free form, or bound to a nanoparticle located at the sample spot, e.g. a particle having a diameter of e.g. about 0.5-20 nm, preferably about 1-5 nm.

For illuminating single molecules at individual sample spots on the support, a light source suitable for multipoint-illumination, e.g. a laser light source may be used. Preferably, the light source is a multipoint light source, e.g. a multipoint laser light source. The light source is capable of providing a plurality of individual illuminated volume elements at the individual sample spots. The volume elements have a size from $10^{-10}$ to $10^{-24}$ I, e.g. from $10^{-12}$ to $10^{-24}$ I. The volume elements may be confocal volume elements or volume elements provided by the evanescent filed obtained by Total Internal Reflection (TIR). Preferably, the volume elements are provided by the evanescent filed obtained by Total Internal Reflection (TIR).

The process of the invention comprises detection of light emitted from single molecules positioned on the support. Preferably, the detected light is emitted from optically detectable labelling groups, particularly from fluorescence labelling groups. The emitted light is subsequently detected with a light detector and correlated with an event associated with a single molecule positioned at an individual spot on the support.

Detection of emitted light may involve detection of lifetime of an excited state, and/or detection of rotational mobility and/or detection of lateral mobility and/or detection of a specific wavelength. Furthermore, it is possible to use Raman, Raman/Antistokes and/or surface-enhanced Raman (SER) based detection methods to identify single molecules. Preferably, the detection of emitted light involves a lifetime detection optionally combined with the detection of a specific wavelength. For example, it has been shown that different components can be discriminated with an accuracy of 0.998 if their mean life times differ by around a nanosecond.

The event to be detected may be caused by e.g. association and/or dissociation of the labelling group with the single molecule to be analysed or by any other event causing a time-dependent change of light emission, e.g. a time-dependent fluorescence change.

Illuminating the volume element, e.g. the confocal volume element excites labelling groups present in the volume so that they emit light, e.g. fluorescent light, which is measured by means of the detector. The pattern of illuminated volume elements may be generated by a matrix of laser dots generated via diffractive optical elements, e.g. as described on WO 2002/097406, the content of which is herein incorporated by reference, or a quantum well laser. Preferably, the light source is a multipoint light source, e.g. a multipoint laser light source. The light source is capable of providing a plurality of individual illuminated volume elements at the individual sample areas suitably by applying appropriate optical elements in the path of the light. The volume elements may have a size from $10^{-10}$ to $10^{-24}$ I, e.g. from $10^{-12}$ to $10^{-21}$ I.

In a preferred embodiment, light is irradiated into the support, whereby an evanescent excitation field is generated by way of internal reflection at the support surface in the region of the molecules to be analysed. Internal reflection at one or more positions of the support surface in the region of the molecules to be analysed, generates an evanescent excitation field which causes excitation of labelling groups present in the respective spots. In an especially preferred embodiment, the detection involves a total internal reflection (TIR), particularly total internal reflection fluorescence (TIRF) detection.

Diffractive optical elements (DOEs) may be used to provide multi-point illumination on the support. DOEs may also be used in detection methods involving internal reflection, e.g. by introducing a diffractive optical element into the exciting light beam in a TIR(F) setup.

According to the present invention, light emitted from the single molecules is detected with a light detector which comprises a plurality of detection pixels aligned with a matrix of sample spots on the support. Preferably, the detector is a multipoint single photon avalanche detector (SPAD). It combines high sensitivity over a broad spectral range, e.g. 350-900 nm with a high time resolution of e.g. ≤1 ns, which is advantageous when the lifetime of an excited fluorescent state is to be used for molecular analysis.

For an exact identification of a labelling group, e.g. a fluorescent labelling group, the lifetime of the excited state is preferably determined together with a wavelength-specific emission. The lifetime is preferably in the range between 1-6 ns. From a combination of parameters selected from lifetime, characteristic count rate per molecule (determined by wavelength-dependent laser intensity), excitation coefficient (e.g. about $10^5$/M cm), quantum yield (e.g. 0.3-0.9), and/or wavelength-dependent detector sensitivity, the identification of the labelling group can be carried out without application of specific wavelength-dependent emission filters.

Further, it is preferred to carry out a pulsed excitation of the single molecules to be analysed in order to eliminate or reduce straylight caused by Raleigh and Raman scattering as well as formation of triplet states and photon bleaching. A preferred pulse excitation time is less than 1 ns, e.g. about 50-500 ps.

The diameter of individual detection pixels on the detector is usually about 0.5 μm-50 μm. The individual detection pixels are separated by a distance (i.e. the pixel pitch length), the length of which is at least the pixel diameter, preferably at least about 2 times, more preferably at least about 3-10 times, the diameter of the detection pixel. Preferably, the distance between pixels on the detector is about 2-200 μm, more preferably about 4-150 μm.

As outlined above, an optical projection of the detection pixels is formed on the support. The optical projections on the supports are e.g. about 10-200 times or about 40-120 times smaller than the size of the detection pixels on the detector. Hence, the optical projections usually have a diameter of about 20 nm to about 1 μm, preferably about 100-600 nm. The distance between the centers of individual detection pixel projections on the support (i.e. the projection pitch length) is preferably at least about 2 times, preferably about 3-10 times, in particular at least 3 times or at least 5 times the diameter of a detection pixel projection. Basically, the distance between individual spots or the support should match the distance between each detection pixel of the detector. The projection pitch length is preferably equivalent to the sample spot distance, e.g. from about 50-5000 nm, preferably from about 150-3000 nm.

In a preferred embodiment, the process of the invention is used for the sequencing of single nucleic acid molecules. In this embodiment, the process preferably comprises the steps:
 providing at an individual sample spot of the support (i) a single nucleic acid molecule, (ii) a nucleic acid-synthesizing enzyme molecule and/or a nucleic acid degrading enzyme molecule, and
 (iii) fluorescence labelled nucleotide building blocks in free form and/or incorporated into the nucleic acid molecule, conducting an enzymatic reaction, wherein nucleotide building blocks are incorporated into and/or cleaved off from said single nucleic acid molecule, and individually determining the base sequence of the nucleic acid molecule on the basis of the time-dependent fluorescence change, caused when nucleotide building blocks are incorporated into and/or cleaved off from said single nucleic acid molecule.

Both incorporation of nucleotide building blocks into a nucleic acid molecule and cleaving off nucleotide building blocks from a nucleic acid molecule may cause a time-dependent change in the fluorescence emission of labelling groups.

In embodiments involving sequencing by degradation, a nucleic acid-degrading enzyme molecule is contacted with a nucleic acid molecule to be sequenced having incorporated labelling groups, particularly fluorescence labelling groups.

In embodiments involving sequencing by elongation, a nucleic acid-synthesizing enzyme molecule is contacted with a nucleic acid molecule to be sequenced having annealed thereto a primer and free nucleotide building blocks with labelling groups, particularly fluorescence labelling groups.

In one embodiment, a nucleic acid synthesizing enzyme molecule and/or a nucleic acid degrading enzyme molecule may be immobilized, e.g. on the support, or on a nanoparticle positioned on the support. In another embodiment, the nucleic acid molecule to be sequenced may be immobilized, e.g. on the support or on a nanoparticle positioned on the support.

In one embodiment, the present application relates to a process for sequencing an individual nucleic acid molecule, comprising the following steps:
 (a) providing at least one nucleic acid-synthesizing enzyme molecule in immobilized form, a circular or linear nucleic acid template, a primer annealed to said template or capable of annealing to said nucleic acid template, and fluorescence-labelled nucleotide building blocks,
 (b) generating a nucleic acid molecule complementary to the sequence of the nucleic acid template molecule having incorporated said nucleotide building blocks in a primer elongation catalyzed by said immobilized nucleic acid-synthesizing enzyme molecule,
 (c) optionally contacting said generated nucleic acid molecule with a nucleic acid-degrading enzyme molecule and cleaving off individual nucleotide building blocks from said generated nucleic acid molecule in a nuclease digestion catalyzed by said nucleic acid-degrading enzyme molecule, and
 (d) determining the base sequence of said nucleic acid template molecule on the basis of the time-dependent fluorescence change,
caused when nucleotide building blocks are incorporated during primer elongation and/or cleaved off during nuclease digestion.

In a further embodiment, the present application relates to a process for sequencing an individual nucleic acid, comprising the following steps:
 (a) providing a nucleic acid-synthesizing enzyme, a circular or linear nucleic acid template molecule in immobilized form, a primer annealed to said template or capable of annealing to said nucleic acid template, and fluorescence-labelled nucleotide building blocks,
 (b) generating a nucleic acid molecule complementary to the sequence of said immobilized nucleic acid template having incorporated said nucleotide building blocks in a primer elongation catalyzed by said nucleic acid-synthesizing enzyme molecule,
 (c) optionally contacting said generated nucleic acid molecule with a nucleic acid degrading enzyme molecule and cleaving off individual nucleotide building blocks from said generated nucleic acid molecule in a nuclease digestion catalyzed by said nucleic acid-degrading enzyme molecule, and
 (d) determining the base sequence of said nucleic acid template on the basis of the time-dependent fluorescence change, caused when nucleotide building blocks are incorporated during primer elongation and/or cleaved off during nuclease digestion.

In a further embodiment, the present application relates to a process, comprising the following steps:
(a) providing at least one nucleic acid-degrading enzyme molecule in immobilized form, a nucleic acid molecule comprising fluorescence-labelled nucleotide building blocks,
(b) contacting said nucleic acid-degrading enzyme molecule with said nucleic acid molecule, and cleaving off individual nucleotide building blocks from said nucleic acid molecule in a nuclease digestion, catalyzed by said nucleic acid-degrading enzyme molecule, and
(c) determining the base sequence of said nucleic acid molecule on the basis of the time-dependent fluorescence change, caused when nucleotide building blocks are cleaved off during nuclease digestion.

In a further embodiment, the present application relates to a process for sequencing an individual nucleic acid, comprising the following steps:
(a) providing at least one nucleic acid molecule comprising fluorescence-labelled nucleotide building blocks in immobilized form and a nucleic acid-degrading enzyme molecule,
(b) contacting the nucleic acid molecule with the nucleic acid-degrading enzyme molecule and cleaving off individual nucleotide building blocks from said nucleic acid molecule in a nuclease digestion catalyzed by said nucleic acid-degrading enzyme molecule, and
(c) determining the base sequence of said nucleic acid molecule on the basis of the time-dependent fluorescence change, caused when nucleotide building blocks are cleaved off during nuclease digestion.

The process of the invention is a support-based multiplex sequencing method which enables a multiplicity of individual nucleic acid molecules to be sequenced. This is achieved by providing a reaction space comprising a nucleic acid molecule to be sequenced, and a nucleic acid-degrading and/or nucleic acid-synthesizing enzyme for determining in parallel time-dependent fluorescence change in a plurality of nucleic acid synthesis and/or degradation reactions. The process is preferably carried out in the form of a parallel high throughput single molecule analysis.

In a preferred embodiment, a nucleic acid-synthesizing enzyme molecule is provided in immobilized form. A nucleic acid-degrading enzyme molecules may also be present in immobilized form or in free form. In still other embodiments, hybrids and/or conjugates of nucleic acid-synthesizing enzyme molecules and nucleic acid-degrading enzyme molecules, e.g. genetic fusions and/or conjugates linked by bi-functional linker molecules, may be used.

In a further preferred embodiment, a support having a multiplicity of nucleic acid molecules in immobilized form is provided. In this embodiment, nucleic acid synthesizing enzyme molecules and/or nucleic acid-degrading enzyme molecules or hybrids and/or conjugates thereof may be used in a free form.

The support used for said process may be any planar or structured support. Preferably, the support is planar. Examples of suitable support materials are glass, quartz, plastic, metals, semimetals such as silicon, for example, metal oxides such as silicon dioxide, for example, or composites comprising said materials. The support may, at least in the region of the sample spots, have sufficient optical transparency and suitable surface properties for irradiation with fluorescence excitation light or/and backscatter of fluorescence emission light through the support or for evanescence-based fluorescence detection. In principle, the support may also have any design, as long as a reaction space can be formed which enables individual nucleotide building blocks to be incorporated into and cleaved off progressively from the nucleic acids contacted with said support in a liquid reaction mixture.

The process of the present invention may be carried out in a single reaction space which is formed across the support or the portion thereof, on which the enzyme or nucleic acid molecules are immobilized. Alternatively, the process may also be carried out in a multiplicity of separate reaction spaces across the support, wherein the separate reaction spaces are not in communication with each other, at least during certain steps of the process. Multiple separate reaction spaces may e.g. be formed by nano- and/or microwells and/or nano- or microspots on the support.

The enzyme or nucleic acid molecules may be immobilized via covalent or noncovalent interactions. For example, high-affinity interactions between the partners of a specific binding pair, for example biotin/streptavidin or avidin, hapten/anti-hapten antibody, sugar/lectin, etc., can mediate immobilizing of the polypeptides or nucleic acids. Thus it is possible to couple biotinylated enzyme or nucleic acid molecules to streptavidin-coated surfaces. Alternatively, the enzyme or nucleic acid molecules may also be immobilized via adsorption. Thus enzyme or nucleic acid molecules modified by incorporation of alkane thiol groups, may bind to metallic supports, e.g. supports made of gold. Yet another alternative is covalent immobilization in which it is possible to mediate enzyme or nucleic acid molecule binding via reactive silane groups on a silica surface.

According to the invention, at least one single molecule is analysed. Preferably a plurality of single molecules is analysed. These molecules are located at the sample spots on the support. They are in contact with a sample liquid, which contains the free reaction partners. Thereby, one or more reaction spaces are defined. Preferably at least 100, particularly preferably at least 1000, and particularly preferably at least 10000, and up to more than $10^6$, molecules may be analysed on a single support, e.g. a single planar support.

The molecules to be analysed, e.g. the enzyme or nucleic acid molecules are applied to specific spots on the support surface, for example by contacting a diluted solution of biotinylated molecules with a support, only particular regions of which are coated with streptavidin. In embodiments where the nucleic acid-degrading enzyme molecules are immobilized, they may be co-immobilized with nucleic acid-synthesizing enzyme molecules, i.e. both types of enzyme molecules are bound in the same spots of the support surface.

The nucleic acid molecule whose sequence is to be determined may be selected, for example, from DNA molecules such as genomic DNA fragments, cDNA molecules, plasmids, etc., or else from RNA molecules such as mRNA molecules. The nucleic acid molecule may originate from genomic or expression libraries, generated from cells or organisms, e.g. eukaryotic or prokaryotic cells or organisms. The process of the present invention allows parallel sequencing of a plurality of different nucleic acid template molecules, e.g. at least 10, 100, 1.000 or 10.000 and up to 100.000, $10^6$ or $10^7$ or even more different nucleic acid molecules.

Preferably, the nucleic acid molecules to be sequenced are single-stranded nucleic acid molecules in a linear or circular form, e.g. in a covalently linked circular form. In order to obtain a circular nucleic acid template, a linear nucleic acid molecule may be subjected to a circularization procedure and optionally a strand-separation procedure during sample preparation. Circularization may be effected by ligation according to known protocols, e.g. using DNA or RNA ligases. In some embodiments, an adaptor and/or identifier molecule, i.e. a nucleic acid molecule of known sequence, may be coupled to the nucleic acid molecule.

The nucleic acid molecules are preferably from 20 to 100000 nucleotides, particularly preferably 20 to 50000, more preferably from 20 to 10000, 20 to 5000 nucleotides, particularly preferably from 50 to 2000 or from 100 to 1000 nucleotides, in length. The sequence determination may comprise nucleic acid elongation and/or nucleic acid degradation. The sequencing process includes one or more sequencing cycles.

The nucleic acid-synthesizing enzyme molecules are capable of elongating a primer annealed to a nucleic acid template molecule. Preferably, primer elongation is carried out by progressively incorporating individual nucleotide building blocks at the 3'-terminus of a growing nucleic acid chain, wherein a nucleic acid molecule complementary to the sequence of the circular nucleic acid template is generated. The nucleic acid-synthesizing enzymes are selected from polymerases capable of a template specific nucleic acid polymerization, preferably from DNA polymerases and RNA polymerases, e.g. natural or modified polymerases, including thermostable DNA polymerases.

Specific examples of suitable DNA polymerases include Taq polymerases, exonuclease-deficient Taq polymerases, *E. coli* DNA polymerase I, Klenow fragment, reverse transcriptase, φ29-related polymerases including wild-type φ29 polymerase and derivatives of such polymerases, such as exonuclease-deficient forms, T7 DNA polymerase, T5 DNA polymerase, an RB69 polymerase and others.

The nucleic acid-degrading enzyme molecules are capable of progressively cleaving off individual nucleotide building blocks from a nucleic acid molecule. Preferably exonucleases, more preferably single-strand exonucleases which degrade in the 3'→5' direction or in the 5'→3' direction are used. Exonucleases which are particularly preferably used are 3'→5' exonucleases such as *E. coli* exonuclease I and *E. coli* exonuclease III, and 5'→3' exonucleases such as T7 exonuclease, *E. coli* exonuclease II and *E. coli* exonuclease VIII. Further, the exonuclease activities of various polymerases, e.g. the Klenow fragment, Taq polymerase or T4 polymerase may be used.

The nucleic acid-synthesizing enzyme molecules are contacted with a linear or circular nucleic acid template molecule, e.g. a single-stranded DNA or RNA molecule, and a primer molecule annealed to the nucleic acid template molecule or capable of annealing thereto. The primer molecule is preferably a single-stranded nucleic acid or nucleic acid analogue molecule having a free 3'-end which can be extended by an enzymatic reaction catalyzed by the immobilized nucleic acid-synthesizing enzyme molecules. The length of the primer molecule is selected to allow effective annealing to the template under reaction conditions. Usually, the length of the primer molecule is at least 8, at least 10, at least 12 or at least 15 nucleotides and e.g. up to 20, 25, 50 or 100 nucleotides, or even higher. In some embodiments, the primer is resistant against digestion by nucleic acid-degrading enzyme molecules, e.g. by incorporating nucleotide analogue building blocks and/or linkages between nucleotide building blocks, which are stable against degradation. In other embodiments, the primer is sensitive against digestion by nucleic acid-degrading enzyme molecules.

The sequence of the primer is selected in that it effectively anneals under reaction conditions to the template molecule. For instance, the primer may be a universal degenerated primer capable of statistically annealing to unknown nucleic acid sequences. In other embodiments, the primer may be capable of annealing to a known sequence portion of the nucleic acid template molecule. In this embodiment, a known adaptor and/or identifier sequence may be incorporated into the nucleic acid template molecule. The primer may be unlabelled or comprise fluorescent labelling groups.

Further, the presence of nucleotide building blocks carrying at least one fluorescent labelling group is required. Preferably, each different nucleotide building block (A, G, C, T/U) contains a different fluorescent labelling group. The fluorescent labelling groups may be selected from known fluorescent labelling groups used for labelling biopolymers, particularly nucleic acids, such as, for example, fluoresceins, rhodamines, oxazines, for example Evoblue or Gnothis Blue, phycoerythrin, Cy3, Cy5, IR dyes or derivatives thereof, etc.

The nucleotide building blocks may carry (i) a fluorescence labelling group which remains with the building block when the building block is incorporated into a nucleic acid molecule during a primer elongation catalyzed by a nucleic acid-synthesizing enzyme molecule, and/or (ii) a fluorescence labelling group which is cleaved off from the building block when the building block is incorporated into a nucleic acid molecule during a primer elongation catalyzed by a nucleic acid-synthesizing enzyme molecule. Fluorescence labelling groups remaining with the building block are preferably attached to the α-phosphate group, to the sugar and/or to the nucleobase group. Preferably, fluorescence labelling groups remaining with the building block are attached to the nucleobase, e.g. via a linker which may have a chain-length of up to 15, preferably of 10-12 carbon atoms, optionally including heteroatoms, e.g. N, O or S atoms. Fluorescence labelling groups which are cleaved off when the building block is incorporated into a nucleic acid molecule may be attached to a terminal phosphate group, e.g. of a hexa-, penta-, tetra- or triphosphate building block such as the γ-phosphate group of a triphosphate building block. In certain embodiments, building blocks are selected which contain both (i) a fluorescence labelling group remaining after incorporation and (ii) a fluorescence labelling group cleaved off during incorporation. In this case, fluorescence groups capable of interacting with each other, e.g. by quenching and/or energy transfer, may be selected.

The nucleic acid molecules to be sequenced will contain fluorescent labelling groups in case the nucleic acid molecule is subjected to direct sequencing using a nucleic acid-degrading enzyme molecule. On the other hand, the nucleic acid molecule to be sequenced my not contain fluorescent labelling groups, if the nucleic acid molecule is used as a template in a primer elongation.

The process of the present invention may involve a step of generating nucleic acid molecules having incorporated nucleotide building blocks in a primer elongation catalyzed by the nucleic acid-synthesizing enzyme molecules and/or a second step of cleaving off individual nucleotide building blocks from the generated nucleic acid molecules catalyzed by nucleic acid-degrading enzyme molecules. Dependent on the type of fluorescence labels, nucleic acid sequence determination may be carried out during primer elongation and/or during degradation.

Sequence determination during the primer elongation involves the use of nucleotide building blocks carrying a fluorescence-labelling group which is cleaved off from the building block when it is incorporated into a nucleic acid molecule. In this case, a time-dependent fluorescence change caused by cleaving off the fluorescence-labelling group from the nucleotide building block may be determined. Sequence determination during nucleic acid degradation involves the use of a nucleotide building block, which carries a fluorescence-labelling group which remains with the building block when it is incorporated into a nucleic acid molecule. Progressive cleavage of individual nucleotide building blocks from the nucleic acid molecules causes a time-dependent change of fluorescence when the labelled nucleotide building block is liberated from the nucleic acid molecule. In certain embodiments, it is also possible to carry out a sequence determination during elongation and degradation, i.e. when using nucleotide building blocks, which both carry a fluorescence-labelling group remaining with the building block and a fluorescence-labelling group which is cleaved off from the building block when the building block is incorporated into a nucleic acid molecule. In this embodiment, both fluorescent groups may be the same or different.

In some embodiments, the method of the invention involves one or more cycles of nucleic acid-synthesis and nucleic acid-degradation in order to determine the base sequence of a nucleic acid molecule template. The nucleic acid synthesis involves an elongation of the primer annealed to the nucleic acid template molecule catalyzed by the nucleic acid-synthesizing enzyme molecule, wherein a nucleic acid molecule complementary to the sequence of the nucleic acid template is generated. In the next step, the generated nucleic acid molecule is degraded by a nucleic acid-degrading enzyme molecule.

When a nucleotide building block is incorporated into an elongated nucleic acid molecule, a time dependent change in the fluorescence may occur, which can be detected as indicated above. Preferably, the incorporation of the nucleotide building blocks into the elongated nucleic acid molecule is associated with a detectable increase in the fluorescence, preferably with a transient increase in the fluorescence. For example, nucleotide building blocks may be used which carry a fluorescent labelling group on the portion of the molecule which is cleaved off when the building block is incorporated into the primer, e.g. on the γ-phosphate group.

When a nucleotide building block is cleaved off from the synthesized nucleic acid molecule, a time-dependent change of fluorescence may be determined due to the interaction of fluorescent labelling groups incorporated in nucleic acid strands with neighbouring groups, for example with chemical groups of the nucleic acids, in particular nucleobases such as, for example, G, or/and neighbouring fluorescent labelling groups, and these interactions leading to a change in fluorescence, in particular in fluorescence intensity, compared to the fluorescent labelling groups in "isolated" form, owing to quenching processes or/and energy transfer processes. The removal by cleavage of individual nucleotide building blocks alters the overall fluorescence, for example the fluorescence intensity of an immobilized nucleic acid strand, and this change is a function of the removal by cleavage of individual nucleotide building blocks, i.e. a function of time.

In certain embodiments association of a labelled nucleotide with the biomolecule complex is detected by measuring polarisation of the emitted photons. The polarisation of excited states' photons is changed by the rotational movement of the light emitting nucleotide labels and can be used for identifying free moving contra bound labelled nucleotides in the polymerisation process.

This time-dependent change in fluorescence during elongation and/or degradation may be recorded in parallel for a multiplicity of nucleic acid molecules and correlated with the base sequence of the individual nucleic acid strands. Preference is given to using those fluorescent labelling groups which, when incorporated in the nucleic acid strand, are, at least partially, quenched so that the fluorescence intensity is increased after the nucleotide building block containing the labelling group or a neighbouring building block causing quenching has been removed by cleavage.

During incorporation and/or removal of individual nucleotide building blocks, it is possible to measure a change in fluorescence intensity of the nucleic acid strand or/and the incorporated or cleaved-off nucleotide building block, owing to quenching processes or energy transfer processes. This change in fluorescence intensity with time depends on the base sequence of the nucleic acid strand studied and can therefore be correlated with the sequence.

The complete sequence of the nucleic acid molecule may be determined by using a mixture of nucleotide building blocks, labelled on all four different bases, for example on A, G, C and T, or on combinations of two or three different bases. It is possible, where appropriate, to attach to the nucleic acid strand to be studied also a "sequence identifier", i.e. a labelled nucleic acid of known sequence, for example by enzymatic reaction using ligase or/and terminal transferase, so that at the start of sequencing initially a known fluorescence pattern and only thereafter the fluorescence pattern corresponding to the unknown sequence to be studied is obtained.

The detection comprises irradiating light into the support, preferably by means of a laser, or by another suitable light source, in order to cause excitation of the fluorescent labelling groups. It is possible, in this connection, to use one or more laser beams, for example an expanded laser beam, having a cross section of approx. 1-20 mm, or/and multiple laser beams. The detection preferably comprises a multi-point fluorescence excitation by lasers, for example a dot matrix of laser dots generated via diffraction optics (cf. WO 2002/097406) or a quantum well laser.

Fluorescence emission of a plurality of nucleic acid strands may be detected in parallel using a detector matrix which comprises, for example, an electronic detector matrix, for example a CCD camera, a CMOS detector matrix, e.g. a CMOS camera, or an avalanche photodiode matrix. The detection may be carried out in such a way that fluorescence excitation and detection are carried out in parallel on all nucleic acid strands studied. A possible alternative to this is to study in several steps in each case a portion of the nucleic acid strands. Preference is given to carrying out the detection on fluorescence light which is emitted essentially orthogonally from the support surface through the reaction space or through the support body.

The detection may be carried out, for example, by means of confocal single molecule detection, for example by fluorescence correlation spectroscopy, which involves exposing a very small, preferably confocal, volume element, for example from $10^{-21}$ to $10^{-10}$ l, to the excitation light of a laser, or another suitable light source, which light excites the receptors present in this measuring volume so that the latter emit fluorescence light, the fluorescence light emitted from said measuring volume being measured by means of a photodetector and the change in the measured emission with time being correlated with the concentration of the analyte, so that it is possible to identify, at an appropriately high dilution, individual molecules in said measuring volume. Details of the procedure and of the apparatus used for detection can be found in the disclosure of the European patent 0679251. The confocal determination of single molecules is furthermore described in Rigler and Mets (Soc. Photo-Opt. Instrum. Eng. 1921 (1993), 239 ff.) and Mets and Rigler (J. Fluoresc. 4 (1994) 259-264).

Alternatively or additionally, detection may also be carried out by way of time-resolved decay measurement, called "time gating", as described, for example, by Rigler et al., "Picosecond Single Photon Fluorescence Spectroscopy of Nucleic Acids", in: "Ultrafast Phenomenes", D. H. Auston, Ed., Springer 1984. Here, the fluorescent molecules are excited in a measuring volume followed by, preferably at a time interval of ≥100 ps, opening a detection interval on the photodetector. In this way it is possible to keep background signals generated by Raman effects sufficiently low so as to enable single molecules to be detected in an essentially interference-free manner.

The invention also relates to an apparatus for analysing at least one individual single molecule, e.g. for sequencing at least one nucleic acid molecule, comprising:
(a) a support comprising at least one sample spot, wherein said spot has a diameter in the range of about 1 nm-20 nm and the distance between individual spots is at least about 10 times, preferably about 20-500 times the diameter of the spot, for positioning a single molecule to be analysed on an individual spot,
(b) a light source which provides at least one individual illuminated volume element at a sample spot on the support, for individually illuminating a single molecule at an individual spot,
(c) a light detector which comprises at least one detection pixel wherein said detection pixel has a diameter in the range of about 0.5 µm-50 µm and the distance between said detection pixels is at least about 2 times, preferably about 3-10 times the diameter of the detection pixel, for individually detecting light emitted from a single molecule at an individual spot, and
(d) means for correlating the detected signals from individual detection pixels with an event associated with a single molecule positioned on an individual spot,
wherein an optical projection of a detection pixel on the support has a diameter in the range of about 100 nm-5 µm and wherein an individual sample spot is aligned to the projection of a single detection pixel on the support, particularly to the center of the projection of a single detection pixel on the support.

The invention further relates to an apparatus for analysing a plurality of individual single molecules or a plurality of individual nucleic acid molecules in parallel, comprising:
(a) a support comprising a plurality of sample spots, wherein said spots have a diameter in the range of about 1-20 nm and the distance between individual spots is at least about 10 times, preferably about 20-500 times the diameter of the spot, for positioning a single molecule to be analysed on an individual spot,
(b) a light source which provides a plurality of individual illuminated volume elements at the spots on the support, for individually illuminating single molecules at individual spots,
(c) a light detector which comprises a plurality of detection pixels, wherein said detection pixels on the detector have a diameter the range of about 0.5 µm-50 µm and the distance between said detection pixels is at least about 2 times, preferably about 3-10 times the diameter of the detection pixel, for individually detecting light emitted from a single molecule at an individual spot, and
(d) means for correlating the detected light from individual detection pixels with an event associated with a single molecule positioned on an individual spot,
wherein the spots may comprise areas on the support surface, e.g. areas of metal, semi-metal or silane.

Metal spots may be prepared by vapour deposition of metals such as Au, Ag, Al, Cr, Ni and others, which are vapourized on a support covered by a grid mask, which may be produced by electrobeam lithography or equivalent technologies. The size of holes in the grid mask may correspond to the size of the spots on the support surface. Preferably, the hole diameter in the grid mask is 5 nm or less. Alternatively, the spots on the support may be prepared by site-specific deposition of nanoparticles, e.g. having a size of 2-10 nm, by zeptoliter precision pipetting of particles on the support, particularly on a support having a planar surface. The particles may have a surface selected from metal such as Au, Ag, Al, Cr, Ni or others, semi-metal or silane. Alternatively, the particles can be made from quantum dots, which may have fluorescence properties. The spot surface areas on the support and/or the particles may be modified by biotin and/or streptavidin or other affinity reagents as described above.

The sample spots on the support are preferably aligned to the center of the projection of individual detection pixels. Adjustment of the alignment between sample spots and detection pixel projections may be carried out by a nanometer precision piezo-adjustment element in a detector-driven feedback loop. The adjustment tolerance between the center of a sample spot and the center of a detection pixel projection is preferably about 5 nm or less, about 2 nm or less or about 1 nm or less.

The process of the invention and the apparatus of the invention may be employed, for example, in the analysis of genomes and transcriptomes or in differential analyses, for example studies regarding the difference in the genome or transcriptome of individual species or organisms within a species. Particularly preferred is the determination of the frequency and/or distribution of individual subsequences within a population of sequences, e.g. of at least 10, at least $10^2$, at least $10^3$ or at least $10^4$ individual sequences.

In a preferred embodiment, the process of the invention and the apparatus of the invention may be employed in the analysis of quasi-species sequences (cf. M. Eigen et al., "Molecular Quasi Species", *J. Phys. Chem.* 92, December 1988, 6881-6891; M. Eigen & C. Biebricher, "Role of Genome Variation in Virus Evolution", in *RNA Genetics*, Vol. 3: Variability of RNA Genomes; CRC Press 1988; M. Eigen & R. Winkler-Oswatitsch, "Statistical Geometry on Sequence Space", in *Molecular Evolution: Computer Analysis of Protein and Nucleic Acid Sequences*, Academic Press, 1990, M. Eigen et al., "The Hypercycle-Coupling of RNA and Protein Biosynthesis in the Infection Cycle of an RNA Bacteriophage", *Biochemistry* 30, November 1991, 11005-11018, M. Eigen, "Viral Quasispecies", *Scientific American*, July 1993, 42-49, E. Domingo et al. "Quasispecies and RNA Virus Evolution: Principles and Consequences", *Landes Bioscience Madame Curie Database,* 2000 and references recited therein).

By means of single molecule sequencing, the distribution of individual sequences within a population of organisms within a species or within a population of cells within an organism may be determined. For example, populations of organisms, such as bacteria or viruses, or populations of cells, such as spermatozoa, do not contain identical genetic information in certain sequences of their genomes. Instead, there are distinct individual sequences (corresponding to so-called quasi-species or sub-species) present, which differ in one or several, e.g. 2, 3 or 4 nucleotides, over a given length. The present invention now allows exact determination of individual variant sequences by means of single molecule sequencing, particularly by means of repeated cycles of single molecule sequencing of individual variants. Thereby, the frequency and distribution of individual sub-sequences within a population of organisms, e.g. viral or bacterial organisms, or a population of cells, e.g. spermatozoa, may be determined. By means of this information, the distribution of sub-species within a given population of organisms or a population of cells may be exactly determined. This allows—in case of pathogenic organisms such as bacteria or viruses—an improved diagnosis and therapy, e.g. by detecting the presence or absence of drug-resistant mutations. In case of cells such as spermatozoa, an improved genetic analysis, e.g. by detecting the presence or absence of certain genotypes, may be carried out.

The accuracy of the sequencing can even be further improved by sequencing both the so called + and − strand of a target double stranded DNA. By sequencing both the + and the − strand it is possible to achieve an accuracy of having one erroneous nucleotide reading out of $10^6$ analysed nucleotides. DNA consists of two strands of nucleic bases. Each nucleic base type in one strand is complementary to the base type of the other strand, each complementary strand referred to as the + and − strand. Below we use the term "base pairing" to describe that one DNA strand is complementary to the base type of the other DNA strand so that A and T and C and T shall always be situated opposite to each other at the same base number. Furthermore we refer to the complementary DNA strands as "+ strand" and "− strand".

According to an embodiment of the present invention it is possible to analyse the + strand as well as the − strand of a single DNA molecule. According to this embodiment the nucleic acid target comprises of the two complementary strands of a single double stranded nucleic acid. Thus, the two complementary strands are referred to as the + and − strand. Accordingly, in one embodiment the nucleic acid target comprises of the + and − strand.

The primary accuracy, p, is here defined as the probability that the method correctly identifies and reports the type (any of A, T, C or G) of a single base in a single DNA molecule using only a single strand (a + or − strand).

In case both the + strand and the − strand of a single DNA molecule are read in accordance to one embodiment of the present invention the primary accuracy of the method is increased as compared with the situation in which only a single strand of a single DNA molecule is analysed. Using the a priori knowledge of the rule of base pairing the statistical accuracy in determination of each base type is increased, as further described below.

When measuring two complementary bases in a double stranded DNA molecule the only logically correct result shall be such that the base types obeys the rule of base pairing. In this way erroneous measurements of a base can be identified and discarded. The only event that cannot be identified is the event that the method incorrectly determines both complementary bases in such a way that the erroneous result obeys the rule of base pairing. The probability of an event as defined the previous sentence is $(1-p)^2$. Hence, the probability that the method correctly determines a base in a double stranded DNA (a nucleic acid target comprising both + and − strand) is $1-(1-p)^2$ which is equal to P(one base is correctly determined by the method using double stranded DNA) $=p(2-p)(6)$.

In FIG. 6 the primary accuracy, p, is shown together with the probability of correct read-out of one base when both strands of a DNA are measured.

Furthermore, the figures below are intended to illustrate the present invention.

The pixel number of a detector is preferably about 100 to about 500.000. The pixel diameter on the detector is preferably about 1-20 μm and the detector pitch length (i.e. the distance between individual pixels on the detector) is about 2-200 μm.

In the following, Table 2 shows preferred pixel diameter and pitch length sizes on the detector.

TABLE 2

| Pixel no. | 1024 | 4096 | 16384 | 409600 |
|---|---|---|---|---|
| Pixel diameter (μm) | 20 | 10 | 5 | 1 |
| Pitch length (μm) | 100 | 50 | 25 | 5 |

Figure 1:
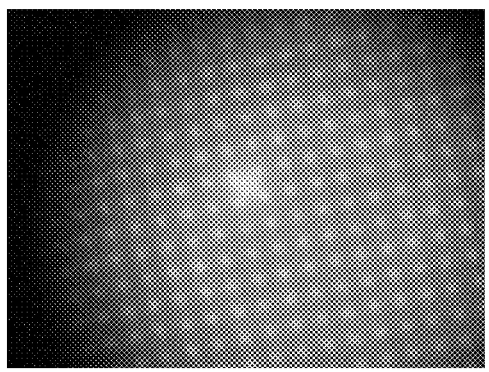
FIG. 1 shows a laser point matrix with confocal illuminated volume elements generated by a diffractive optical element as described on WO 2002/097406.
Figure 2:
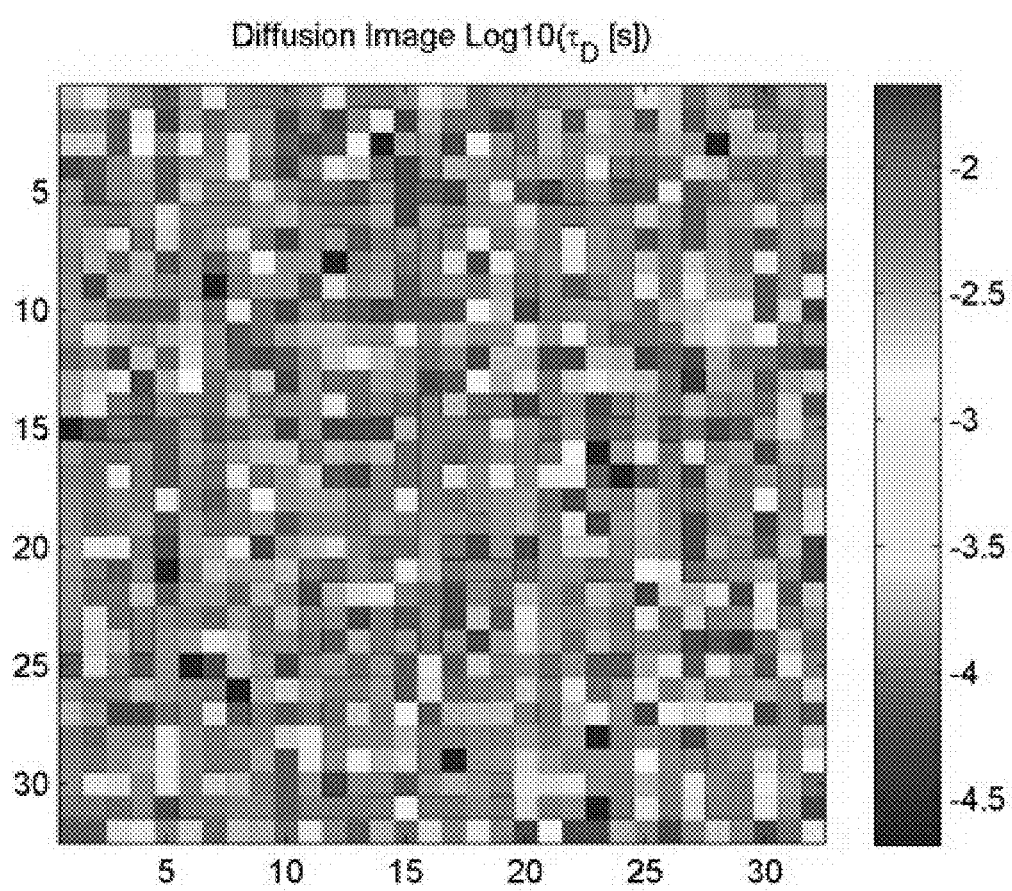
FIG. 2 shows a 1024-pixel SPAD detector. SPAD detectors combine high sensitivity over a broad spectral range of e.g. 350-900 nm with high-time resolution (≤1 ns).
Figure 3:
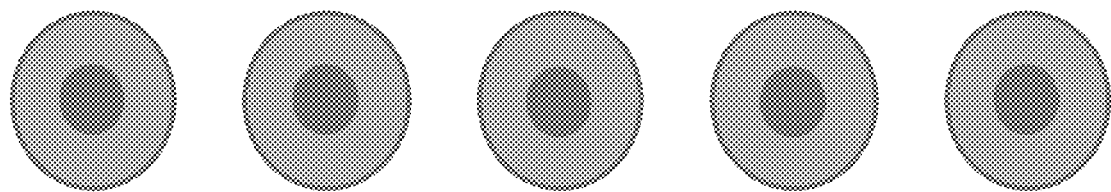

FIG. 3 shows alignment of sample spots (black) in the center of optical projections of detection pixels (grey) on the support.

Table 3 demonstrates the relationship of sample spot diameter (SD), pixel projection diameter (PD) and sequencing accuracy (A). Further sample spot distance which is equivalent to pixel projection distance (projection pitch) and pixel magnification (ratio of pixel diameter to pixel projection diameter) are shown. The sequencing accuracy may be calculated as follows: $A=\exp-(SD/PD)^2$

TABLE 3

| | Sample spot diameter SD (nm) | Pixel projection diameter PD (nm) | Sample spot distance (nm) | Accuracy A |
|---|---|---|---|---|
| 100× Magn. | 10 | 200 | 1000 | 0.9975 |
| 60× Magn. | 10 | 333 | 1665 | 0.9990 |

Alignment of detector pixel matrix and sample spot matrix is preferably carried out by a nanometer precision x-y piezo-adjustment in a detector-driven feedback loop (Physik Instrumente GmbH & Co. KG, Karlsruhe, Germany).

Figure 4:
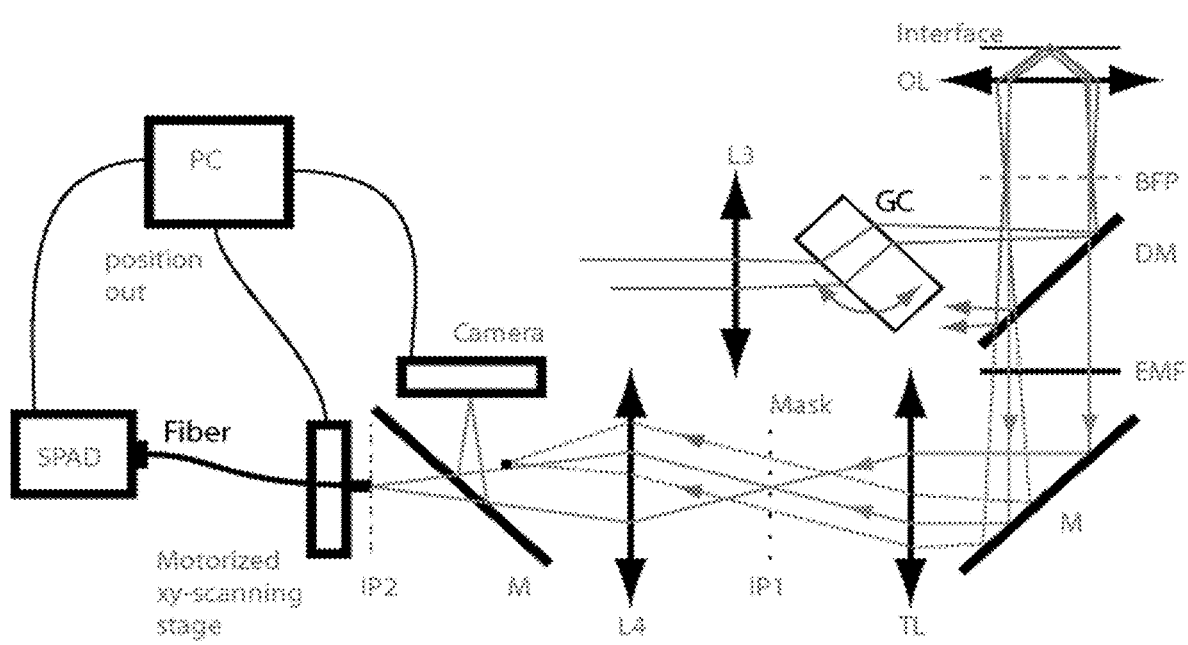

FIG. 4 shows an objective type of internal reflection (TIR) set up with laser based excitation. A collimated laser beam is focused in the back focus plane of a high NA objective. The collimated laser beam is totally reflected by the glass surface of the illuminated area. Fluorescent molecules at the surface are excited to fluorescence in the evanescent field which decays exponentially with the distance from the surface. With introduction of a diffractive optical element after the lens focusing the collimated laser beam a multiplicity of laser beams can be generated which are reflected by TIR. Together with the pixels of the SPAD matrix and their projection on the TIR surface a multitude of confocal volume elements can be generated.

Abbr. OL objective lens, BFP back focal plan, DM dichroic mirror, DOE diffractive optical element, GC angular beam control, EMF emission filter, SPAD single photon avalanche diode matrix.

Figure 5:
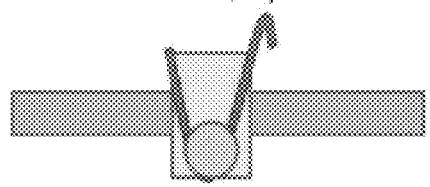
Figure 5:
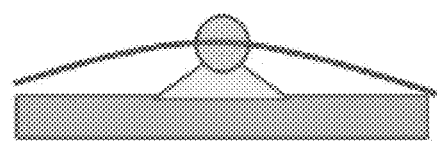

FIG. 5 shows that a TIR(F) setup allows adjustment of the angle of the incoming and totally reflected beam and hence the size of the evanescence field. A volume of a few zeptoliters can be reached particularly with the use of DOE split laser beams. The advantage of a flat surface is the application of free flow on the surface and enzymatic operation on unkinked DNA strands.

Figure 6:
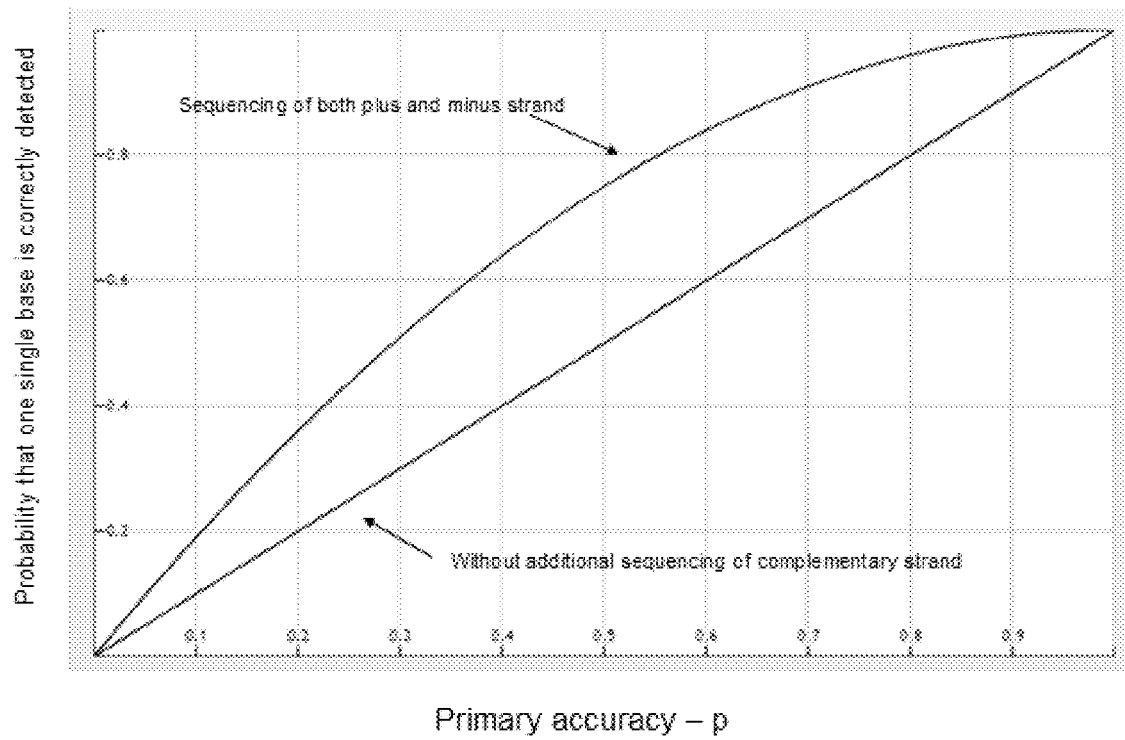

FIG. 6: The primary accuracy, p, is shown together with the probability of correct read out of one base when both strands of a DNA are measured.

The invention claimed is:

1. A process for analyzing a single molecule comprising the following steps:
    (a) providing at least one single molecule to be analyzed positioned at an individual sample spot on a support, wherein said spot has a diameter in the range of about 1-20 nm and the distance between each individual spot is at least about 10 times the diameter of the spot,
    (b) individually illuminating a single molecule at an individual sample spot with a light source, wherein said light source provides at least one illuminated volume element at the sample spot, the at least one illuminated volume element is provided by an evanescent field obtained by total internal reflection (TIR),
    (c) individually detecting light from said single molecule with a light detector, wherein said light detector comprises at least one detection pixel, wherein said detection pixel on the detector has a diameter in the range of about 0.5 µm-50 µm and the distance between each detection pixel is at least about 2 times the diameter of the detection pixel,
    (d) optically projecting said detection pixel onto the support by means of an optical pathway between the light source, the support and the light detector, wherein the optical projection has a diameter in the range of about 100 nm -5 µm and is about 10-200 times smaller than the size of the detection pixel on the detector,
    (e) aligning an individual sample spot on the support, to the optical projection of a single detection pixel such that the center of the individual sample spot is aligned to the projection of the single detection pixel on the support, wherein the distance between individual sample spots on the support is equivalent to the distance between optical projections of detection pixels on the support, and
    (f) detecting light from an individual detection pixel wherein said light results from an event associated with a single molecule positioned on an individual spot.

2. The process for analyzing a single molecule according to claim 1, wherein the distance between individual sample spots on the support is from 50 nm-5000 nm to avoid cross-talk between individual pixels.

3. The process for analyzing a single molecule according to claim 1, wherein said event associated with a single molecule positioned on an individual spot is caused by association or dissociation of a labeling group or a time dependent change of light emission.

4. The process for analyzing a single molecule according to claim 1, wherein said process has an accuracy of at least 99.0% with a single measurement and wherein said measurement is repeated up to 10 times.

5. The process for analyzing a single molecule according to claim 4, wherein said process has an accuracy of 99.9% with a single measurement and wherein said measurement is repeated up to 10 times.

6. The process of claim 1, wherein the detected light is emitted from single molecules comprising detectable labelling groups.

7. The process of claim 1, wherein said single molecule is a single nucleic acid molecule.

8. The process of claim 7, wherein the single nucleic acid molecule is circular, or wherein the single nucleic acid molecule is linear.

9. The process of claim 1, further comprising the steps:
    providing at an individual spot of the support (i) a single nucleic acid molecule, (ii) a nucleic acid-synthesizing enzyme molecule, and (iii) fluorescence labelled nucleotide building blocks in free form,
    conducting an enzymatic reaction, wherein nucleotide building blocks are incorporated into said single nucleic acid molecule, and
    individually determining the base sequence of the nucleic acid molecule on the basis of the time-dependent fluorescence change, caused when nucleotide building blocks are incorporated into said single nucleic acid molecule.

10. The process of claim 9, wherein the nucleic acid-synthesizing enzyme molecule or the nucleic acid-degrading enzyme molecule is in immobilized form.

11. The process of claim 1, wherein the support has a planar surface.

12. The process of claim 1, wherein the support has a surface selected from the group consisting of glass, plastic, metal, quartz, semi-metal, metal oxide and a composite comprising a plurality thereof.

13. The process of claim 1, wherein a sample spot comprises a coated surface area on the support or a particle deposited on the surface of the support.

14. The process of claim 1, wherein the surface of a sample spot and/or of a particle deposited thereon is a metal selected from the group consisting of Au, Ag, Cr, Ni and Al, a semi-metal and a silane.

15. The process of claim 1, wherein the surface of a sample spot and/or of a particle deposited thereon is modified with a capturing reagent selected from the group consisting of biotin, streptavidin and another high-affinity capturing reagent.

16. The process of claim 1, wherein the light detector is selected from the group consisting of a multipoint single photon avalanche detector (SPAD), a CCD camera and a CMOS detector matrix.

17. The process of claim 1, wherein the light detector comprises $10^3$ to $10^6$ individual detection pixels.

18. The process of claim 1, wherein the position of a sample spot relative to a detection pixel is aligned by an adjustment element.

19. The process of claim 1, wherein the light source is a multipoint laser.

20. The process of claim 1, wherein the at least one illuminated volume element is provided by a diffractive optical element.

21. The process of claim 1, wherein a diffractive optical element is introduced into the exciting light beam in a TIR setup.

22. The process according to claim 1, further comprising providing a population of sequences and determining the frequency and/or distribution of subsequences within that population.

23. The method of claim 22, wherein the population of sequences comprises at least 10, at least $10^2$, at least $10^3$, or at least $10^4$ individual members.

24. The process of claim 1, further comprising the steps:
providing at an individual spot of the support (i) a single nucleic acid molecule, (ii) a nucleic acid degrading enzyme molecule, and (iii) fluorescence labelled nucleotide building blocks incorporated into the nucleic acid molecule,
conducting an enzymatic reaction, wherein nucleotide building blocks are cleaved off from said single nucleic acid molecule, and
individually determining the base sequence of the nucleic acid molecule on the basis of the time-dependent fluorescence change, caused when nucleotide building blocks are cleaved off from said single nucleic acid molecule.

25. A process for analyzing single molecules, comprising the following steps:
(a) providing a plurality of single molecules to be analyzed, each positioned at an individual sample spot on a support, wherein said spots have a diameter in the range of about 1-20 nm and the distance between individual spots is at least about 10 times the diameter of the spot,
(b) individually illuminating single molecules at individual spots with a light source by means of an optical pathway between the light source, the support, a light detector, and an objective, wherein said light source provides a plurality of individual illuminated volume elements at the sample spots, and wherein the volume elements are provided by an evanescent field obtained by total internal reflection (TIR),
(c) individually detecting light emitted from said single molecules with said light detector, wherein the light detector comprises a plurality of detection pixels, wherein said detection pixels on the light detector have a diameter in the range of about 0.5 μm -50 μm and the distance between said detection pixels is at least about 2 times the diameter of the detection pixel,
(d) optically projecting said detection pixels onto the support by means of an optical pathway between the light source, the support and the light detector to produce an optical projection, wherein the optical projection has a diameter in the range of about 100 nm -5 μm and is about 10-200 times smaller than the size of the detection pixels on the light detector,
(e) aligning an individual sample spot on the support, to the optical projection of a single detection pixel such that the center of the individual sample spot is aligned to the projection of the single detection pixel on the support, wherein the distance between individual sample spots on the support is equivalent to the distance between optical projections of detection pixels on the support, and
(f) detecting light from an individual detection pixel wherein said light results from an event associated with a single molecule positioned on an individual spot.

26. A process for analyzing a single molecule comprising the following steps:
(a) providing at least one single molecule to be analyzed positioned at an individual sample spot on a support, wherein said spot has a diameter in the range of about 1-20 nm and the distance between each individual spot is at least about 10 times the diameter of the spot,
(b) individually illuminating a single molecule at an individual sample spot with a light source, wherein said light source provides at least one illuminated volume element at the sample spot,
(c) individually detecting light from said single molecule with a light detector, wherein said light detector comprises at least one detection pixel, wherein said detection pixel on the detector has a diameter in the range of about 0.5 μm -50 μm and the distance between each detection pixel is at least about 2 times the diameter of the detection pixel,
(d) optically projecting said detection pixel onto the support by means of an optical pathway between the light source, the support and the light detector, wherein the optical projection has a diameter in the range of about 100 nm -5 μm and is about 10-200 times smaller than the size of the detection pixel on the detector,
(e) aligning an individual sample spot on the support, to the optical projection of a single detection pixel, wherein the distance between individual sample spots on the support is equivalent to the distance between optical projections of detection pixels on the support, and
(f) detecting light from an individual detection pixel wherein said light results from an event associated with a single molecule positioned on an individual spot,
wherein the at least one single molecule to be analyzed is illuminated through an at least partially optically transparent support and wherein emission light emitted through the support is determined, wherein light is emitted through the support and the formation of an evanescent excitation field is caused by internal reflection on the support surface in the region of the illuminated sample spots.

27. The process according to claim 26, wherein the formation of an evanescent excitation field is caused by total internal reflection (TIR).

* * * * *